United States Patent [19]

Kigawa et al.

[11] Patent Number: 5,292,941
[45] Date of Patent: Mar. 8, 1994

[54] METHOD FOR OZONIZING UNSATURATED FATTY ACIDS OR LOWER ALKYL ESTERS THEREOF AND METHOD FOR THE OXIDATIVE DECOMPOSITION OF OZONIZED PRODUCTS

[75] Inventors: Hitoshi Kigawa, Hiratsuka; Hiroshi Yamaya, Fuchu; Yurie Iino, Kawasaki, all of Japan

[73] Assignee: Lion Corporation, Tokyo, Japan

[21] Appl. No.: 966,155

[22] PCT Filed: Aug. 6, 1991

[86] PCT No.: PCT/JP91/01046
§ 371 Date: Jan. 27, 1993
§ 102(e) Date: Jan. 27, 1993

[87] PCT Pub. No.: WO93/02991
PCT Pub. Date: Feb. 18, 1993

[51] Int. Cl.$^5$ ............................................. C07C 51/16
[52] U.S. Cl. ............................................. 562/544
[58] Field of Search ............................................. 562/544

[56] References Cited

U.S. PATENT DOCUMENTS

| | | | |
|---|---|---|---|
| 2,813,113 | 11/1957 | Goebel et al. | 260/406 |
| 3,507,793 | 4/1970 | Mitchell et al. | 252/55 |
| 3,868,392 | 2/1975 | Siclari et al. | 562/544 |
| 4,287,130 | 9/1981 | Dohm et al. | 562/544 |
| 5,095,143 | 3/1992 | Heberer et al. | 562/544 X |

Primary Examiner—Arthur C. Prescott
Attorney, Agent, or Firm—Birch, Stewart, Kolasch & Birch

[57] ABSTRACT

A method for ozonizing an unsaturated fatty acid or a lower alkyl ester thereof is provided as comprising the steps of: supplying an unsaturated fatty acid or a lower alkyl ester thereof as a thin film stream, and passing a gas containing ozone in oxygen or a mixture of oxygen and air or inert gas in the same direction as the flow direction of said thin film stream, thereby achieving gas-liquid contact between the thin film stream of unsaturated fatty acid or lower alkyl ester thereof and the ozone-containing gas. Also provided is a method for oxidative decomposition of the thus ozonized product by contact with ozone-free oxygen gas or air.

11 Claims, 3 Drawing Sheets

METHOD FOR OZONIZING UNSATURATED FATTY ACIDS OR LOWER ALKYL ESTERS THEREOF AND METHOD FOR THE OXIDATIVE DECOMPOSITION OF OZONIZED PRODUCTS

FILED OF THE INVENTION

This invention relates to a method for ozonizing unsaturated fatty acids or lower alkyl esters thereof at their unsaturated bond and a method for oxidative decomposition of the thus ozonized products into short chain monobasic or dibasic acids or esters thereof.

BACKGROUND OF THE INVENTION

It is known in the prior art to cause ozone to act on unsaturated fatty acids such as oleic acid, thereby effecting continuous ozonization of their double bond (Japanese Patent Publication No. 4714/1961 or U.S. Pat. No. 2,813,113 and Japanese Patent Publication No. 9206/1968).

The prior art continuous ozonization methods of unsaturated fatty acids which use an apparatus having a plurality of reaction zones and rely on the counterflow gas-liquid contact process of contacting unsaturated fatty acid solution with ozone-containing gas in a counterflow manner, however, are dangerous because excess ozone can be locally supplied to form peroxides. The counterflow gas-liquid contact process of this type is difficult to quickly remove reaction heat from the apparatus or reactor tower.

German Patent No. 2,713,863 discloses a method for continuously producing an ozonide (or ozonized product) by ozonizing a high molecular weight olefin, oleic acid or linoleic acid in the presence of water and an organic acid or alcohol. Since this method supplies the reactant and an ozone-containing gas in parallel flow relationship, but does not form a thin film flow of the reactant, it is necessary to efficiently remove reaction heat generated during ozonization and to add large amounts of water and organic acid or alcohol for keeping the resulting ozonide (or ozonized product) stable, thus resulting in low yields per unit time. Moreover, although a plurality of static mixers are provided in the reactor tower for mixing organic acid and water, it is difficult to maintain a stable emulsion. As emulsion particles become larger, local heating occurs inevitably.

Also known in the prior art is oxidative decomposition by causing oxygen to act on ozonized products of unsaturated fatty acids (Japanese Patent Publication No. 4717/1961).

Although the oxidative decomposition reaction of ozonized products of unsaturated fatty acids is said to take place at a temperature of 75° to 125° C. according to the Publication, the actual temperature was limited up to 100° C. Thus the oxidative decomposition reaction took a long time, resulting in low yields. If reaction were performed at high temperatures of 100° C. or higher, especially 125° C. or higher, abrupt oxidation would occur, imposing a safety problem. Also, part of the final product could be oxidized into carbon dioxide and water while forming by-products, leaving a problem in yields.

Therefore, there is a need for the development of a commercially advantageous method for the oxidative decomposition of ozonized products of unsaturated fatty acids.

DISCLOSURE OF THE INVENTION

An object of the present invention is to provide a method for ozonizing an unsaturated fatty acid or a lower alkyl ester thereof which ensures efficient removal of reaction heat, safety, and increased yield per unit time in commercial scale production.

Another object of the present invention is to provide a method for oxidative decomposition of an ozonized product of an unsaturated fatty acid or a lower alkyl ester thereof which is capable of effectively and safely oxygenating and decomposing an ozonized product of an unsaturated fatty acid or a lower alkyl ester thereof in a commercial scale.

Making extensive investigations for achieving these objects, the inventors have found that by supplying a solution of an unsaturated fatty acid or a lower alkyl ester thereof as a thin film stream, and contacting a gas containing ozone in oxygen gas or a mixture of oxygen gas and air or inert gas with the thin film stream, the unsaturated fatty acid or lower alkyl ester thereof can be efficiently ozonized without a risk of excess ozone supply, that is, in a safe manner, and removal of reaction heat is easy due to the fact that the unsaturated fatty acid or lower alkyl ester thereof undergoing ozonization reaction forms a thin film stream. Particularly when the reactant is an unsaturated fatty acid lower alkyl ester and the ozone-containing gas is passed in parallel flow relationship, a thin film stream of the ester is readily available whereupon ozonization reaction takes place concurrently, the reactant itself can be a solvent, and an ozonized product shows little increase in viscosity, all contributing to an improvement in production efficiency from a commercial standpoint. Further, mixing the unsaturated fatty acid or lower alkyl ester thereof with a saturated fatty acid or lower alkyl ester thereof ensures that a uniform thin film stream be formed and ozonization reaction proceed uniformly.

The inventors have also found that the thus ozonized product of unsaturated fatty acid or lower alkyl ester thereof can be safely and efficiently oxygenated and decomposed in a commercial scale by continuously contacting the ozonized product with ozone-free oxygen gas or air at a temperature of 100° to 150° C., preferably in a reactor having previously added thereto an oxidatively decomposed product of an unsaturated fatty acid or lower alkyl ester thereof as a diluent.

Particularly when the ozonized product subject to oxidative decomposition is an ozonized product of an unsaturated fatty acid lower alkyl ester, unlike an ozonized product of an unsaturated fatty acid, 100° C. becomes the critical temperature below which the rate of conversion is very low, but above which the rate of conversion is significantly increased. Then temperatures of 100° to 150° C. allow oxidative decomposition to proceed at a high rate of conversion. Despite the reaction at such high temperatures, there occur no problems with respect to safety and undesirable formation of by-products, and reaction heat resulting from oxidative decomposition can be promptly removed. As a result, there is little risk of local heating which can occur with the use of fatty acids as the reactant possibly disturbing agitation, and no loss is observed in the yield of the end product.

It is to be noted that the problems of the prior art including a lowering of production efficiency per unit time and potential abnormal reaction are solved when an oxidatively decomposed product of an unsaturated fatty acid lower alkyl ester is used as a diluent and reaction is continuously effected in a reactor having the diluent previously added thereto, because accumulation of the ozonized product of the reactant in the reactor to an undesirably high concentration is avoided, and for this reason, even at high temperatures of 100° to 150° C., reaction proceeds safely at a high rate of conversion without forming a by-product so that the reaction rate is further drastically increased. Therefore, when an ozonized product of an unsaturated fatty acid lower alkyl ester is subject to effective oxidative decomposition reaction within a short time in a commercial scale, more benefits are obtained in that the end product is obtained in higher yields.

Therefore, the present invention provides a method for ozonizing an unsaturated fatty acid or a lower alkyl ester thereof, characterized by comprising the steps of: supplying an unsaturated fatty acid or a lower alkyl ester thereof as a thin film stream, and passing a gas containing ozone in oxygen or a mixture of oxygen and air or inert gas in the same direction as the flow direction of said thin film stream, thereby achieving gas-liquid contact between the thin film stream of unsaturated fatty acid or lower alkyl ester thereof and the ozone-containing gas.

The present invention also provides a method for the oxidative decomposition of the thus ozonized product of an unsaturated fatty acid or a lower alkyl ester thereof, characterized by comprising the step of contacting the ozonized product with ozone-free oxygen gas or air.

Preferred embodiments of the present invention will become evident from the following description.

BEST MODE FOR CARRYING OUT THE INVENTION

Figure 1:
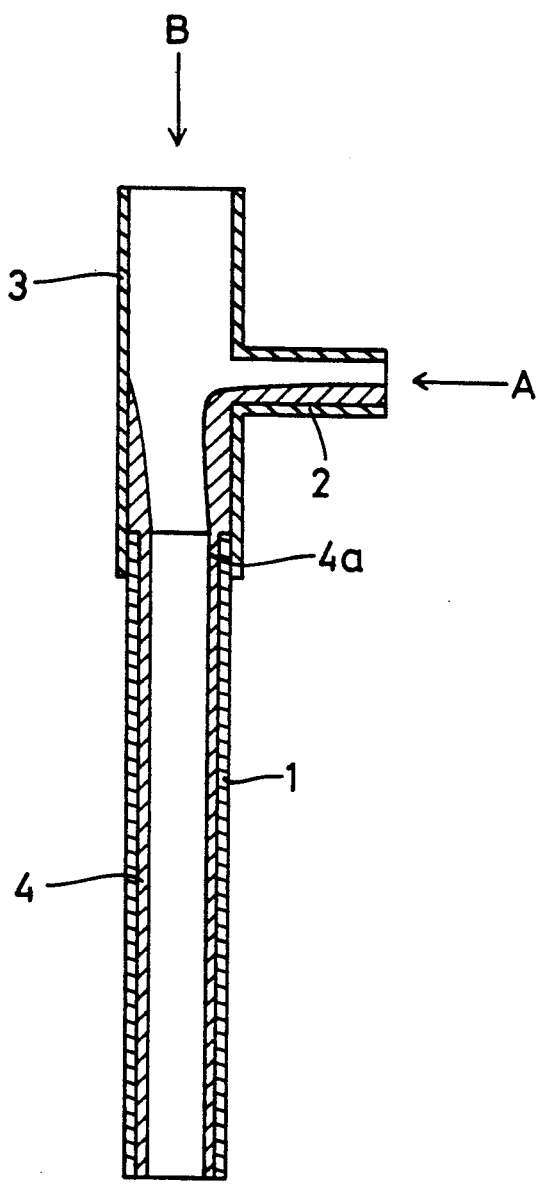
FIG. 1 is a schematic cross section showing one exemplary apparatus use in the ozonization method of the present invention.

The method for ozonizing an unsaturated fatty acid or a lower alkyl ester thereof according to the present invention involves the steps of supplying an unsaturated fatty acid or a lower alkyl ester thereof as a thin film stream, and contacting the thin film stream with a gas containing ozone in oxygen gas or a mixture of oxygen gas and air or inert gas.

The unsaturated fatty acids used herein include unsaturated fatty acids having an unsaturated bond, especially unsaturated fatty acids containing 1 to 3 unsaturated bonds and having 16 to 18 carbon atoms, such as palmitoleic acid, oleic acid, linoleic acid, and linolenic acid. Since the unsaturated fatty acids require a substantial amount of solvent to form a thin film stream, esters of the unsaturated fatty acids with lower alcohols are preferably used.

Preferred unsaturated fatty acids or lower alkyl esters thereof used herein are of the general formula (1):

RCOOR'  (1)

wherein R is a monovalent hydrocarbon group containing 1 to 3 double bonds and having 15 to 17 carbon atoms, and R' is a hydrogen atom or an alkyl group having 1 to 4 carbon atoms.

These unsaturated fatty acids or lower alkyl esters thereof themselves can serve as a solvent in forming a thin film stream or require only a small amount of solvent to form a thin film stream, although it is preferred, if their viscosity is high, to add to them a saturated fatty acid or a lower alkyl ester thereof of the general formula (2):

R"COOR'  (2)

wherein R' is as defined above and R" is an alkyl group having 7 to 19 carbon atoms. It is especially useful to add small amounts of the lower alkyl esters of saturated fatty acids, for example, lower alkyl esters of such saturated fatty acids as lauric acid, myristic acid, palmitic acid, stearic acid, and arachic acid. By adding these saturated fatty acid lower alkyl esters to the unsaturated fatty acid lower alkyl esters, there are obtained mixtures having a reduced viscosity enough to produce a uniform thin film of appropriate thickness in forming a thin film stream.

Preferably, the unsaturated fatty acid or lower alkyl ester thereof and the saturated fatty acid or lower alkyl ester thereof are mixed in a weight ratio of the former to the latter of from 100:0 to 70:30, more preferably from 99:1 to 70:30. A too large proportion of the saturated fatty acid or lower alkyl ester thereof would sometimes result in a too low viscosity at optimum reaction temperature (10° to 50° C.) and rather fail to form a uniform thin film stream.

In the practice of the invention, a thin film stream is formed from the unsaturated fatty acid or lower alkyl ester or if desired, a solution of the unsaturated fatty acid or lower alkyl ester in a solvent such as the saturated fatty acid or lower alkyl ester mentioned above, or an alcohol, hydrocarbon, or halogenated hydrocarbon and the thin film stream is contacted with an ozone-containing gas.

The ozone-containing gas used herein is a gas containing ozone in oxygen or a mixture of oxygen and air or an inert gas such as carbon dioxide and nitrogen. The ozone content of the ozone-containing gas preferably ranges from 0.1 to 7% by volume, more preferably from 0.1 to 5% by volume, most preferably from 0.3 to 4% by volume. Inter alia, 0.3 to 4% by volume, especially 0.3 to 3% by volume is preferred for reaction heat and reaction efficiency. Too higher ozone concentrations would sometimes be detrimental to reaction control. In turn, too lower ozone concentrations would sometimes to detrimental to reaction efficiency.

Where the ozone-containing gas is a mixture of oxygen and air or inert gas containing ozone, the mixing proportion of oxygen to air or inert gas is preferably from 100:500 to 100:20, especially from 100:200 to 100:30 in volume ratio.

The thin film stream is formed by passing the ozone-containing gas in parallel flow to the reactant solution containing the unsaturated fatty acid or lower alkyl ester thereof. The ozone-containing gas is preferably passed at a flow velocity of 10 to 100 m/sec., especially 20 to 80 m/sec.

At this point, the ozone-containing gas may be passed in direct contact with the thin film stream. It is also possible to flow oxygen, air or an inert gas such as carbon dioxide and nitrogen as a coolant gas in parallel flow relationship to the thin film stream and flow the ozone-containing gas adjacent to the coolant gas. When the coolant gas interveness between the thin film stream and the ozone-containing gas in parallel flow relationship, ozone must diffuse through the coolant gas stream before it can react with the thin film stream, offering the advantages of suppressed reaction temperature rise and mild reaction. Understandably, the flow velocity of the coolant gas is preferably the same as the flow velocity of the ozone-containing gas.

For practicing the method of the present invention, an apparatus as shown in FIG. 1 may be used. Illustrated in FIG. 1 is a cylindrical reactor 1 which at an upper end is provided with a gas inlet tube 3 having a reactant inlet tube 2 branched therefrom. A reactant solution A containing an unsaturated fatty acid or lower alkyl ester thereof is supplied through the reactant inlet tube 2 and allowed to flow along the interior surface of the gas inlet tube 3 and then the interior surface of the reactor 1 under gravity while an ozone-containing gas B is introduced at a predetermined velocity through the gas inlet tube 3. As a result, a thin film stream 4 of the reactant solution A is formed on the interior surface of the reactor 1 while it is being ozonized. When oxygen, air or an inert gas such as carbon dioxide and nitrogen is passed as the coolant gas as mentioned above, a stream of ozone-containing gas is defined at the center and a coolant gas stream is formed so as to enclose the ozone-containing gas stream. The reactor used herein may be a double cylindrical reactor, multiple cylindrical reactor or the like as well as the above-mentioned single cylindrical reactor, that is, the reactor is not limited to the illustrated one.

The thickness of the thin film stream 4 is not restrictive although the thin film stream preferably has a thickness of up to 3 mm, especially up to 2 mm on the reactant supply side (an upper portion 4a in the illustrated reactor). The lower limit of film thickness is usually 0.05 mm.

Preferably, the ozone in the ozone-containing gas and the unsaturated fatty acid or lower alkyl ester thereof in the thin film stream have a molar ratio of from 0.1:1 to 1.3:1, especially from 0.2:1 to 1.1:1. Where the molar ratio is equal to or above 1:1, the unsaturated fatty acid or lower alkyl ester thereof in the thin film stream can be completely ozonized through a single stage of gas-liquid contact reaction. However, where the molar ratio is below 1:1, which means a relatively low ozone amount, the unsaturated fatty acid or lower alkyl ester thereof is not completely ozonized, leaving unreacted unsaturated fatty acid or lower alkyl ester thereof. In this case, the procedure of recycling the reactant solution which has been partially ozonized, but contains unreacted unsaturated fatty acid or lower alkyl ester thereof to form a thin film stream again and contacting it with ozone-containing gas is repeated until the unsaturated fatty acid or lower alkyl ester thereof in the thin film stream is completely ozonized.

Figure 2:
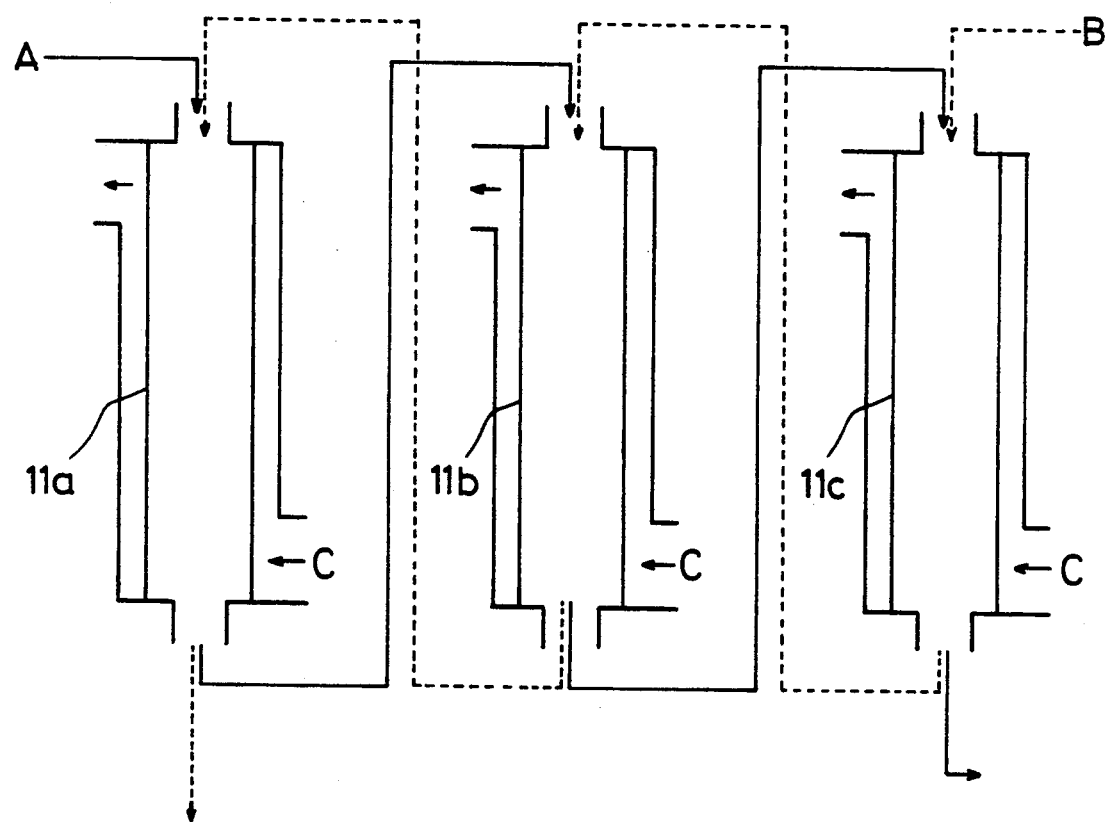
FIG. 2 is a schematic cross section showing another exemplary apparatus used in the ozonization method of the present invention.

This procedure may be embodied using an apparatus as shown in FIG. 2. The apparatus includes a plurality of (three in the figure) juxtaposed cylindrical reactors 11a, 11b, 11c wherein as shown by solid lines, a reactant solution A containing an unsaturated fatty acid or lower alkyl ester thereof is admitted into the first reactor 11a through its upper end to thereby form a thin film stream on the interior wall of the reactor 11a, the reactant solution A outflowing from the lower end of the first reactor 11a is admitted into the second reactor 11b through its upper end to thereby form a thin film stream again, and the reactant solution A outflowing from the lower end of the second reactor 11b is admitted into the third reactor 11c through its upper end. On the other hand, an ozone-containing gas B is, as shown by broken lines, admitted into the third reactor 11c through its upper end, the ozone-containing gas B outflowing from the lower end thereof is admitted into the second reactor 11b through its upper end, and the ozone-containing gas B outflowing from the lower end thereof is admitted into the first reactor 11a through its upper end. In this way, the unsaturated fatty acid or lower alkyl ester thereof in the thin film stream A is reacted with ozone. It is to be noted that the apparatus is designed such that a coolant C such as cooling water is supplied around the respective reactors 11a, 11b and 11c for removing reaction heat.

The number of reactors is not limited to the illustrated embodiments and may be two or four or more. A plurality of stages may be provided until ozonization is complete.

Reaction is preferably carried out at 10° to 50° C., especially at 20° to 45° C. Ozone is liable to thermal decomposition at temperatures above 50° C. whereas at temperatures below 10° C., reaction can proceed, but the reaction product would cause the thin film stream to increase its viscosity to such an extent as to disturb thin film formation. Since the reaction between unsaturated fatty acid or lower alkyl ester thereof and ozone is exothermic, reaction heat should be removed so that the reaction temperature may not exceed 50° C. The supply of unsaturated fatty acid or lower alkyl ester thereof as a thin film stream according to the invention allows for easy removal of reaction heat. By arranging cooling jackets about the periphery of reactors as shown in FIG. 2, for example, external cooling can be easily provided for removing reaction heat.

Understandably, the reaction time depends on the ozone concentration, the feed velocity of ozone-containing gas and reactant solution and the like, but it is usually as short as within one minute after gas-liquid contact.

The above-mentioned method supplies the unsaturated fatty acid or lower alkyl ester thereof as a thin film stream so that very effective gas-liquid contact with ozone is ensured, eliminating the drawbacks of the prior art including a lowering of production efficiency per unit time, removal of reaction heat, and possible formation of peroxides. Therefore, the present method is an advantageous method for producing ozonized products of unsaturated fatty acids or lower alkyl esters thereof in a commercially acceptable scale.

Understandably, the thus obtained ozonized products may be subject to oxidative decomposition with oxygen gas into monobasic or dibasic acids in accordance with methods as disclosed in Japanese Patent Publication Nos. 4717/1961 and 252/1967, which can find application in a wide variety of areas including flavor and polymer areas.

Preferred as the oxidative decomposition method is a method of contacting ozonized products as prepared above with ozone-free oxygen gas or air.

Especially desirable ozonized products are ozonized ones of unsaturated fatty acid lower alkyl esters.

Figure 3:
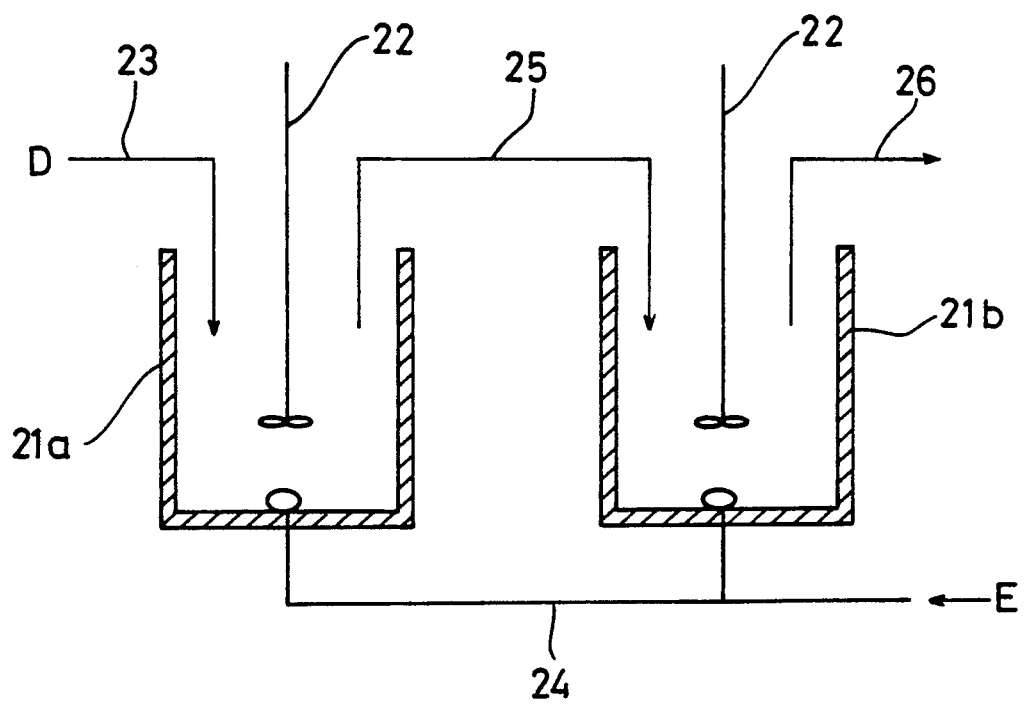
FIG. 3 is a schematic cross section showing one exemplary apparatus used in the oxidative decomposition method of the present invention.

When ozonized products are oxygenated and decomposed with ozone-free oxygen gas or air, this oxidative decomposition reaction may be effected using an apparatus as shown in FIG. 3. The apparatus includes a two stage serial tank type reactor having serially arranged reactors 21a, 21b. The reactors 21a, 21b are equipped with agitators 22, respectively, and a reactant inlet tube 23 is extended to an opening of the first reactor 21a. A reactant solution D is gradually supplied through the reactant inlet coduit 23 so that the solution may flow down through the reactor 21a under gravity while ozone-free oxygen gas or air E is introduced at a predetermined velocity through a gas inlet conduit 24 connect to the bottom of the reactors 21a, 21b. The reaction solution in the first reactor 21a is transferred to the second reactor 21b through a reaction solution transfer conduit 25 whereupon it is again contacted with ozone-free oxygen gas or air E in the reactor 21b. Then the end product is withdrawn through the product transfer conduit 26. Understandably, the reactor used herein may be a combination of reaction towers such as cap towers and perforated plate towers as well as the multi-stage serial tank type reactor illustrated herein and is not limited to the illustrated apparatus. Although the two stage apparatus is illustrated, the apparatus may have three or multiple stages or even a single stage as the case may be.

Preferably, the ozonized product which is a starting solution herein is gradually introduced into the reactor, for example, at an admission rate of 20 to 200 gram/hour, especially 50 to 150 gram/hour for a 300-ml reactor vessel. Understandably, in the multi-stage serial tank type reactor illustrated above, the transfer rate of the reaction solution from reactor to reactor and the withdrawal rate of the product may be within the same range as defined above.

Further, the admission rate of ozone-free oxygen gas or air is preferably from 3 to 30 liter/hour, especially from 5 to 20 liter/hour. It is to be noted that the oxygen pressure is desirably increased somewhat during reaction although atmospheric pressure is acceptable.

It is preferred in the practice of the invention that the molar ratio of ozonized product to ozone-free oxygen gas or air be from 1/1 to 1/10, especially from 1/1.5 to 1/7.5.

Moreover, it is preferred to use a compound of formula (1) defined above, especially an oxidative decomposition product of an unsaturated fatty acid lower alkyl ester as a diluent in such reaction and to previously add this oxidative decomposition product to the reactor because this prevents the ozonized product from accumulating in the reactor at a high concentration.

The amount of the diluent added herein is not critical although effective reaction is expected in amounts of at least 10% by weight, preferably at least 30% by weight based on the ozonized product. It is to be noted that the upper limit of the diluent is preferably 200% by weight based on the ozonized produce.

Moreover, oxidative decomposition reaction takes place at high temperatures of 100° to 150° C., preferably 125 to 150° C., more preferably 125° to 135° C. because reaction temperature lower than 100° C. cause reaction to proceed to a less extent and at a low rate and temperatures in excess of 150° C. cause abrupt reaction, both resulting in low yields of the end product.

Understandably, where the reactor used is a multi-stage serial tank type reactor, it is more effective to gradually increase the temperature from the first reactor to the second reactor and then to the third reactor within the above-defined reaction temperature range.

Moreover, the reaction time is generally within 4 to 6 hours although it depends on the reactant solution, feed rate of oxygen gas and other factors.

After the completion of oxidative decomposition reaction, optional hydrolysis or similar treatment is effected, and distillation under vacuum can fractionate a short chain monobasic or dibasic acid as the final product.

In the above-mentioned oxidative decomposition reaction, the use of an ozonized product of an unsaturated fatty acid lower alkyl ester as the starting material allows for safe reaction at high temperatures as compared with the method for oxidative decomposition reaction of an ozonized product of an unsaturated fatty acid, and accordingly results in a higher rate of oxidative decomposition reaction and an increased production efficiency per unit time, thus providing an advantageous method for producing an oxidative decomposition product of an unsaturated fatty acid lower alkyl ester in a commercial scale.

Examples and comparative examples are given below while the present invention is not limited to the following examples.

EXAMPLES 1-5

Methyl oleate and methyl esters of various saturated fatty acids were mixed in the proportion shown in Table 1. Using the apparatus shown in FIG. 1, the ester mixtures were subject to continuous ozonization reaction under the following conditions by passing the ester mixture and ozone-containing oxygen in parallel flow relationship while forming a thin film. The results are shown in Table 1. It is to be noted that analysis of composition and rate of conversion was by GLC.

Ozonizing Conditions

Reactor (cylindrical) length: 2 m
Reactor inner diameter: 2 mm
Reactant feed rate: 1.5 gram/min.
Molar ratio of ozone to methyl oleate: 1.05
Ozone concentration: 3% by volume
Oxygen feed rate: 4N liter/min.
Linear velocity: 33 m/sec.
The reactor was cooled by circulating water/ethylene glycol at various temperature.

Thin Film Forming Conditions

The outer appearance was observed and judged in accordance with the following criterion.
○: uniform, satisfactory
Δ: non-uniform, partial presence of crystals
X: no thin film formed

Reaction Temperature Measurement

The reactor outer wall temperature was measured by a surface thermometer.

TABLE 1

| | | Results of ozonization reaction | | | | |
| --- | --- | --- | --- | --- | --- | --- |
| | | Examples | | | | |
| | | 1 | 2 | 3 | 4 | 5 |
| Ingredient proportion, % | Methyl oleate | 95 | 85 | 70 | 70 | 70 |
| | Methyl laurate | — | — | — | — | 5 |
| | Methyl myristate | — | — | — | 5 | 5 |
| | Methyl palmitate | — | 5 | 10 | 10 | 10 |

TABLE 1-continued

| | | Results of ozonization reaction Examples | | | | |
|---|---|---|---|---|---|---|
| | | 1 | 2 | 3 | 4 | 5 |
| Methyl stearate | | 5 | 10 | 20 | 10 | 10 |
| Methyl arachate | | — | — | — | 5 | — |
| Thin film formation | | ◯ | ◯ | ◯ | ◯ | ◯ |
| Reaction temperature, °C. | | 10 | 27 | 32 | 45 | 15 |
| Rate of conversion, % | | >99 | >99 | >99 | >99 | >99 |

It is evident from the above data that by maintaining a unsaturated fatty acid methyl ester/saturated fatty acid methyl ester ratio=99/1 to 70/30 in weight ratio and a reaction temperature of at least 10° C., a satisfactory thin film is formed and methyl oleate can be reacted in very high yields.

COMPARATIVE EXAMPLES 1-3

Methyl oleate and methyl esters of various saturated fatty acids were mixed in the proportion shown in Table 2. Using an outer jacketed Oldershaw reactor tube, the ester mixture was subjected to continuous ozonization reaction under the following conditions by previously adding the ester mixture to the reactor tube, passing ozone-containing oxygen through the reactor tube from the bottom, and passing the ester mixture from the top (counter flow contact). The results are shown in Table 2.

Ozonizing Conditions

Reactor tower length: 1 m
Reactor tower inner diameter: 30 mm
Reactant feed rate: 1.5 gram/min.
Molar ratio of ozone to methyl oleate: 1.05
Ozone concentration: 3% by volume
Oxygen feed rate: 4N liter/min.
Coolant: water/ethylene glycol

Reaction Temperature Measurement

The temperature was measured by inserting a temperature sensor at 5 cm above from the reactor tower bottom.

TABLE 2

| | | Results of ozonization reaction Comparative Examples | | |
|---|---|---|---|---|
| | | 1 | 2 | 3 |
| Ingredient proportion, % | Methyl oleate | 95 | 85 | 70 |
| | Methyl palmitate | — | 5 | 10 |
| | Methyl stearate | 5 | 10 | 20 |
| Thin film formation | | X | X | X |
| Reaction temperature, °C. | | 63 | 58 | 55 |
| Rate of conversion, % | | 85 | 92 | 95 |

EXAMPLE 6

An ester mixture of methyl oleate and methyl stearate in a weight ratio of 90/10 was subject to ozonization reaction under the conditions reported in Example 1, finding very satisfactory results including formation of a uniform thin film, a reaction temperature of 30° C., and a rate of conversion of higher than 99%

EXAMPLE 7

An ester mixture of methyl linoleate and methyl stearate in a weight ratio of 90/10 was subject to ozonization reaction under the conditions reported in Example 1, finding very satisfactory results including formation of a uniform thin film, a reaction temperature of 35° C., and a rate of conversion of higher than 99%

EXAMPLE 8

An ester mixture of isopropyl oleate and isopropyl stearate in a weight ratio of 90/10 was subject to ozonization reaction under the conditions reported in Example 1, finding very satisfactory results including formation of a uniform thin film, a reaction temperature of 28° C., and a rate of conversion of higher than 99%

EXAMPLES 9-13

Methyl oleate and methyl esters of various saturated fatty acids were mixed in the proportion shown in Table 3. Using the apparatus shown in FIG. 2, the ester mixtures were subject to continuous ozonization reaction under the following conditions while forming a thin film. The results are shown in Table 3. It is to be noted that analysis of composition and rate of conversion was by GLC.

Ozonizing Conditions

Reactor (each) length: 5 m
Reactor inner diameter: 6 mm
Reactant feed rate: 20 gram/min.
Molar ratio of ozone to methyl oleate: 0.25 or 0.5
Recycling number of reaction solution: 2 or 4
Ozone concentration: 2.5% by volume
Oxygen feed rate: 20N liter/min.
Carbon dioxide feed rate: 10N liter/min.
Linear velocity: 20 m/sec.

Thin Film Forming Conditions

In accordance with Examples 1-5.

Reaction Temperature Measurement

A sensor was inserted into the reactor inner wall to measure the temperature at a spacing of 30 cm from the contact of ozone with the reaction solution.

TABLE 3

| | | Results of ozonization reaction Examples | | | | |
|---|---|---|---|---|---|---|
| | | 9 | 10 | 11 | 12 | 13 |
| Ingredient proportion, % | Methyl oleate | 80 | 80 | 70 | 70 | 95 |
| | Methyl myristate | 2 | 2 | 2 | 2 | — |
| | Methyl palmitate | 3 | 3 | 8 | 8 | — |
| | Methyl stearate | 15 | 15 | 20 | 20 | 5 |
| Molar ratio of ozone to methyl oleate | | 0.25 | 0.5 | 0.25 | 0.5 | 0.5 |
| Recycling number of reaction solution | | 4 | 2 | 4 | 2 | 4 |
| Thin film formation | | ◯ | ◯ | ◯ | ◯ | ◯ |
| Reaction temperature, °C. | | 30 | 37 | 27 | 35 | 39 |
| Rate of conversion, % | | >99 | >99 | >99 | >99 | >99 |

EXAMPLES 14-18

Methyl oleate and methyl esters of various saturated fatty acids were mixed in the proportion shown in Table 4. Using the apparatus shown in FIG. 1, the ester mixture were subject to continuous ozonization reaction under the following conditions while forming a thin film. The results are shown in Table 4. It is to be noted that analysis of composition and rate of conversion was by GLC.

Ozonizing Conditions

Reactor length: 2 m
Reactor inner diameter: 6 mm
Reactant feed rate: 20 gram/min.
Molar ratio of ozone to methyl oleate: 1.05
Ozone concentration: 2.5% by volume
Oxygen feed rate: 20N liter/min.
Carbon dioxide feed rate: 10N liter/min.
Linear velocity: 20 m/sec.

Thin Film Forming Conditions

In accordance with Examples 1-5.

Reaction Temperature Measurement

A sensor was inserted into the reactor inner wall to measure the temperature at a spacing of 30 cm from the contact of ozone with the reaction solution.

TABLE 4

| Results of ozonization reaction | | | | | | |
|---|---|---|---|---|---|---|
| | | Examples | | | | |
| | | 14 | 15 | 16 | 17 | 18 |
| Ingredient proportion, % | Methyl oleate | 87 | 80 | 77 | 70 | 95 |
| | Methyl myristate | — | 2 | 2 | 2 | — |
| | Methyl palmitate | 3 | 3 | 3 | 8 | — |
| | Methyl stearate | 10 | 15 | 18 | 20 | 5 |
| Thin film formation | | ○ | ○ | ○ | ○ | ○ |
| Reaction temperature, °C. | | 32 | 34 | 29 | 31 | 48 |
| Rate of conversion, % | | >99 | >99 | >99 | >99 | >99 |

EXAMPLES 19-22

Methyl oleate and methyl esters of various saturated fatty acids were mixed in the proportion shown in Table 5. The ester mixtures were subject to continuous ozonization reaction under the following conditions while forming a thin film. The results are shown in Table 5. It is to be noted that analysis of composition and rate of conversion was by GLC.

Ozonizing Conditions

Reactor length: 5 m
Reactor inner diameter: 6 mm
Reactant feed rate: 6.7 or 10 gram/min.
Molar ratio of ozone to methyl oleate: 1.05
Ozone concentration: 0.3 or 1.2% by volume
Oxygen feed rate: 20N liter/min.
Carbon dioxide feed rate: 10N liter/min.
Linear velocity: 20 m/sec.

Thin Film Forming Conditions

In accordance with Examples 1-5.

Reaction Temperature Measurement

A sensor was inserted into the reactor inner wall to measure the temperature at a spacing of 30 cm from the contact of ozone with the reaction solution.

TABLE 5

| Results of ozonization reaction | | | | | |
|---|---|---|---|---|---|
| | | Examples | | | |
| | | 19 | 20 | 21 | 22 |
| Ingredient proportion, % | Methyl oleate | 87 | 80 | 87 | 80 |
| | Methyl myristate | — | 2 | — | 2 |
| | Methyl palmitate | 3 | 3 | 3 | 3 |
| | Methyl stearate | 10 | 15 | 10 | 15 |
| Reactant feed rate, g/min. | | 10 | 10 | 6.7 | 6.7 |
| Ozone concentration, vol % | | 1.2 | 1.2 | 0.3 | 0.3 |
| Thin film formation | | ○ | ○ | ○ | ○ |
| Reaction temperature, °C. | | 36 | 35 | 27 | 27 |
| Rate of conversion, % | | >99 | >99 | >99 | >99 |

EXAMPLES 23-24

Methyl oleate and methyl esters of various saturated fatty acids were mixed in the proportion shown in Table 6. The ester mixtures were subject to continuous ozonization reaction under the following conditions while forming a thin film. The results are shown in Table 6. It is to be noted that analysis of composition and rate of conversion was by GLC.

Ozonizing Conditions

Reactor length: 5 m
Reactor inner diameter: 6 mm
Reactant feed rate: 20 gram/min.
Molar ratio of ozone to methyl oleate: 1.05
Ozone concentration: 2.5% by volume
Oxygen feed rate: 20N liter/min.
Air feed rate: 10 or 20N liter/min.
Linear velocity: 20 or 27 m/sec.

Thin Film Forming Conditions

In accordance with Examples 1-5.

Reaction Temperature Measurement

A sensor was inserted into the reactor inner wall to measure the temperature at a spacing of 30 cm from the contact of ozone with the reaction solution.

TABLE 6

| Results of ozonization reaction | | | |
|---|---|---|---|
| | | Examples | |
| | | 23 | 24 |
| Ingredient proportion, % | Methyl oleate | 87 | 80 |
| | Methyl myristate | — | 2 |
| | Methyl palmitate | 3 | 3 |
| | Methyl stearate | 10 | 15 |
| Air feed rate, N liter/min. | | 10 | 20 |
| Thin film formation | | ○ | ○ |
| Reaction temperature, °C. | | 42 | 41 |
| Rate of conversion, % | | >99 | >99 |

EXAMPLES 25-28

Methyl oleate and methyl esters of various saturated fatty acids were mixed in the proportion shown in Table 7. The ester mixture were subject to continuous ozonization reaction under the following conditions while forming a thin film. The results are shown in Table 7. It is to be noted that analysis of composition was by GLC.

Ozonizing Conditions

Reactor length: 5 m
Reactor inner diameter: 6 mm
Reactant feed rate: 20 gram/min.
Molar ratio of ozone to methyl oleate: 1.05

Ozone concentration: 2.5% by volume
Oxygen feed rate: 20N liter/min.
Carbon dioxide feed rate: 10N liter/min.
Linear velocity: 20 m/sec.

Examples 25 and 27 used carbon dioxide as a cooling gas and formed a thin film stream in the reactor tube before it was contacted with ozone-containing oxygen. Examples 26 and 28 used a mixture of carbon dioxide and ozone-containing oxygen and carried out ozonization while forming a thin film stream.

Reaction Temperature Measurement

A sensor was inserted into the reactor inner wall to measure the temperature at spacings of 15 cm, 30 cm and 200 cm from the contact of ozone with the reaction solution.

TABLE 7

| Results of ozonization reaction | | | | | |
|---|---|---|---|---|---|
| | | Examples | | | |
| | | 25 | 26 | 27 | 28 |
| Ingredient proportion, % | Methyl oleate | 87 | 87 | 80 | 80 |
| | Methyl myristate | — | — | 2 | 2 |
| | Methyl palmitate | 3 | 3 | 3 | 3 |
| | Methyl stearate | 10 | 10 | 15 | 15 |
| Reaction temperature (°C.) | at a spacing from ozone - reaction solution contact of | | | | |
| | 15 cm | 43 | 50 | 41 | 49 |
| | 30 cm | 38 | 48 | 37 | 46 |
| | 200 cm | 33 | 33 | 32 | 33 |
| Cooling gas passage | | yes | no | yes | no |

EXAMPLES 29-30 AND COMPARATIVE EXAMPLE 4

Methyl oleate or oleic acid (purity higher than 90%) was subject to continuous ozonization reaction under the following conditions while forming a thin film.

Ozonizing Conditions

Reactor length: 2 m
Reactor inner diameter: 2 mm
Reactant feed rate: 1.5 gram/min.
Molar ratio of ozone to methyl oleate or oleic acid: 1.05
Ozone concentration: 3% by volume
Oxygen feed rate: 4N liter/min.
Linear velocity: 33 m/sec.

Next, oxidative decomposition reaction was carried out under the following conditions. It is to be noted that the rate of conversion was calculated by measuring a loss of the ozonized product by $^1$H-NMR technique.

Oxidative Decomposition Conditions

To the apparatus shown in FIG. 3 including two serially arranged tanks each equipped with a stirrer, temperature sensor, and oxygen inlet tube was added 100 grams of an oxidative decomposition product of an ozonized product of a reactant. After the tank interiors were heated to the reaction temperature, the ozonized product of a reactant was introduced at a rate of 75 gram/hour, the reaction solution transferred from the first tank to the second tank at the same rate, and the product withdrawn from the second tank at the same rate. It is to be noted that $O_2$ gas was admitted at 12 liter/hour.

The results are shown in Table 8.

TABLE 8

| | Example | | Comparative Example |
|---|---|---|---|
| | 29 | 30 | 4 |
| Reactant for ozonization | methyl oleate | methyl oleate | methyl oleate |
| Reaction temperature, °C. | 130 | 102 | 95 |
| Rate of conversion, % | 100 | 72 | 21 |

It is seen from the data of Table 8 that an ozonized product of methyl oleate provides a reaction system ensuring satisfactory yields and safety at high temperatures.

EXAMPLES 31-35

Methyl oleate and methyl esters of various saturated fatty acids were mixed in the proportion shown in Table 9. The ester mixtures were subject to continuous ozonization reaction under the following conditions while forming a thin film, and then to oxidative decomposition under the following conditions using air. The results are shown in Table 9. It it to be noted that the rate of conversion was determined by $^1$H-NMR technique.

Ozonizing Conditions

Reactor length: 5 m
Reactor inner diameter: 6 mm
Reactant feed rate: 20 gram/min.
Molar ratio of ozone to methyl oleate: 1.05
Ozone concentration: 3.0% by volume
Oxygen feed rate: 20N liter/min.
Carbon dioxide feed rate: 10N liter/min.
Linear velocity: 20 m/sec.

Oxidative Decomposition Conditions

Same as in Examples 29-30 except that air was used instead of oxygen gas.

TABLE 9

| Results of ozonization reaction | | | | | | |
|---|---|---|---|---|---|---|
| | | Examples | | | | |
| | | 31 | 32 | 33 | 34 | 35 |
| Ingredient proportion, % | Methyl oleate | 80 | 80 | 70 | 70 | 95 |
| | Methyl myristate | 2 | 2 | 2 | 2 | — |
| | Methyl palmitate | 3 | 3 | 8 | 8 | — |
| | Methyl stearate | 15 | 15 | 20 | 20 | 5 |
| Air oxidative decomposition reaction temperature, °C. | | 130 | 110 | 130 | 110 | 100 |
| Residence time, hour | | 4 | 5.5 | 4 | 5.5 | 7 |
| Rate of conversion, % | | 100 | 100 | 100 | 100 | 100 |

We claim:
1. A method for ozonizing an unsaturated fatty acid or a lower alkyl ester thereof, characterized by comprising the steps of:
   supplying an unsaturated fatty acid or a lower alkyl ester thereof as a thin film stream, and
   passing a gas containing ozone in oxygen or a mixture of oxygen and air or inert gas in the same direction as the flow direction of said thin film stream, thereby achieving gas-liquid contact between the thin film stream of unsaturated fatty acid or lower alkyl ester thereof and the ozone-containing gas.

2. The method of claim 1 wherein the thin film stream of unsaturated fatty acid or lower alkyl ester thereof and the ozone-containing gas are in direct contact.

3. The method of claim 1 which further comprises the step of passing a cooling gas of oxygen, air or inert gas between the thin film stream of unsaturated fatty acid or lower alkyl ester thereof and the ozone-containing gas in parallel flow relationship.

4. The method of claim 1 wherein the unsaturated fatty acid or lower alkyl ester thereof is a compound of the general formula:

$$RCOOR' \qquad (1)$$

wherein R is a monovalent hydrocarbon group containing 1 to 3 double bonds and having 15 to 17 carbon atoms, and R' is a hydrogen atom or an alkyl group having 1 to 4 carbon atoms.

5. The method of claim 1 wherein a mixture of an unsaturated fatty acid or a lower alkyl ester thereof and a compound of the general formula:

$$R''COOR' \qquad (2)$$

wherein R" is an alkyl group having 7 to 19 carbon atoms, and R' is a hydrogen atom or an alkyl group having 1 to 4 carbon atoms is supplied as the thin film stream.

6. The method of claim 1 wherein the thin film stream is 0.05 to 3 mm thick.

7. The method of claim 1 wherein the ozone-containing gas contains 0.1 to 7% by volume of ozone.

8. The method of claim 1 wherein the ozone in the ozone-containing gas and the unsaturated fatty acid or lower alkyl ester thereof in the thin film stream are in a molar ratio of from 0.1:1 to 1.3:1.

9. The method of claim 1 wherein the step of contacting the unsaturated fatty acid or lower alkyl ester thereof with the ozone-containing gas having a lower molar ratio than the acid or ester is repeated a plurality of stages until the unsaturated fatty acid or lower alkyl ester thereof is completely ozonized.

10. A method for the oxidative decomposition of an ozonized product of an unsaturated fatty acid or a lower alcohol thereof, characterized by comprising the step of contacting an ozonized product of an unsaturated fatty acid or a lower alkyl ester thereof resulting from the method of claim 1 with ozone-free oxygen gas or air.

11. The method of claim 8 wherein the reaction temperature is 100° to 150° C.

* * * * *